United States Patent
Lam et al.

(10) Patent No.: US 9,459,190 B2
(45) Date of Patent: Oct. 4, 2016

(54) FUEL TANK CONTAMINANT PREDICTION

(71) Applicant: AIRBUS OPERATIONS LIMITED, Bristol (GB)

(72) Inventors: Joseph K-W Lam, Bristol (GB); Franklin Tichborne, Bristol (GB); Simon Masters, Bristol (GB); David Parmenter, Bristol (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 978 days.

(21) Appl. No.: 13/667,669

(22) Filed: Nov. 2, 2012

(65) Prior Publication Data

US 2013/0124107 A1    May 16, 2013

(30) Foreign Application Priority Data

Nov. 11, 2011    (GB) .................................. 1119499.0

(51) Int. Cl.
| | |
|---|---|
| *G01N 33/22* | (2006.01) |
| *G01F 23/22* | (2006.01) |
| *B64D 37/00* | (2006.01) |
| *B67D 7/08* | (2010.01) |
| *B67D 99/00* | (2010.01) |
| *B64D 47/00* | (2006.01) |
| *G06F 17/40* | (2006.01) |
| *G06F 19/00* | (2011.01) |

(Continued)

(52) U.S. Cl.
CPC ................. *G01N 7/00* (2013.01); *B64D 37/32* (2013.01); *G01F 23/22* (2013.01); *G01N 33/22* (2013.01); *G01N 33/2835* (2013.01); *G06F 15/00* (2013.01); *B64D 37/00* (2013.01); *B64D 47/00* (2013.01); *B67D 7/08* (2013.01); *B67D 99/00* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | |
|---|---|---|---|
| 4,082,511 | A | 4/1978 | Bedford |
| 4,304,132 | A | 12/1981 | Snaper |

(Continued)

FOREIGN PATENT DOCUMENTS

| | | | |
|---|---|---|---|
| CN | 103106552 A | * | 5/2013 |
| EP | 2175420 A1 | | 4/2010 |

(Continued)

OTHER PUBLICATIONS

Search Report corresponding to GB 1119499.0, dated Feb. 24, 2012.

(Continued)

*Primary Examiner* — Edward Cosimano
(74) *Attorney, Agent, or Firm* — Hauptman Ham, LLP

(57) ABSTRACT

A method for predicting a quantity of a contaminant in a fuel tank at the end of a time period, the method comprising the steps of: determining a quantity of the contaminant in the fuel tank at the start of the time period; determining at least one operating condition of the fuel tank during the time period; using information relating to the at least one operating condition of the fuel tank to generate a predicted quantity of the contaminant accumulated in the fuel tank during the time period; and calculating, based upon the quantity of the contaminant at the start of the time period and the predicted quantity of the contaminant accumulated during the time period, a predicted quantity of the contaminant at the end of a time period.

20 Claims, 3 Drawing Sheets

(51) Int. Cl.
*G01N 7/00* (2006.01)
*G01N 33/28* (2006.01)
*B64D 37/32* (2006.01)
*G06F 15/00* (2006.01)

(56) References Cited

U.S. PATENT DOCUMENTS

| | | | |
|---|---|---|---|
| 4,389,889 A | 6/1983 | Larson | |
| 5,333,498 A * | 8/1994 | Brackett | B67D 7/08 73/198 |
| 5,487,300 A * | 1/1996 | Brackett | B67D 7/08 73/201 |
| 7,287,425 B2 * | 10/2007 | Lagergren | G01F 23/2962 73/290 V |
| 7,768,646 B1 | 8/2010 | Mentzer et al. | |
| 8,096,177 B2 * | 1/2012 | Burris | G01F 23/2962 73/290 R |
| 8,171,786 B2 * | 5/2012 | Burris | G01F 23/2962 73/290 V |
| 2005/0284218 A1 * | 12/2005 | Lagergren | G01F 23/2962 73/290 V |
| 2005/0289021 A1 * | 12/2005 | Lagergren | G06Q 10/087 705/28 |
| 2006/0204803 A1 * | 9/2006 | Yamaguchi | H01M 8/04186 429/413 |
| 2009/0126481 A1 * | 5/2009 | Burris | G01F 23/2962 73/290 V |
| 2009/0217753 A1 | 9/2009 | Burris | |
| 2010/0086172 A1 * | 4/2010 | Venkoparao | G06T 7/0004 382/100 |
| 2012/0204980 A1 * | 8/2012 | Nishizawa | F02M 37/0082 137/561 R |

FOREIGN PATENT DOCUMENTS

| | | |
|---|---|---|
| EP | 2520909 A1 | 11/2012 |
| EP | 2175420 B1 * | 2/2013 |
| EP | 2592003 A1 * | 5/2013 |
| EP | 2592003 B1 * | 2/2015 |
| WO | WO 2011/064903 A1 * | 6/2011 |

OTHER PUBLICATIONS

Extended European Search Report for EP 12 19 1644 dated Mar. 5, 2013.

* cited by examiner

# FUEL TANK CONTAMINANT PREDICTION

RELATED APPLICATIONS

The present application is based on, and claims priority from, British Application Number 1119499.0, filed Nov. 11, 2011, the disclosure of which is hereby incorporated by reference herein in its entirety.

FIELD OF THE INVENTION

The present invention relates to a method for predicting a quantity of a contaminant in a fuel tank and to apparatus for predicting a quantity of a contaminant in a fuel tank.

BACKGROUND OF THE INVENTION

Over time, fuel tanks may become contaminated as contaminants are introduced into a fuel system. Fuel tank contaminants may include any solid, liquid or gas which is undesirable in a fuel tank environment. Some examples of common contaminants in a fuel tank include water (both dissolved and free or suspended), ice, microbial or fungal contamination, oil, debris and gaseous contaminants such as oxygen, hydrogen and $CO_2$.

Contaminants may be introduced into a fuel tank via its vent system. Alternatively contaminants may be introduced through an inlet when fuel is introduced into the tank. Contaminants may accumulate in stationary tanks, for example storage tanks or generator fuel tanks, or in vehicle fuel tanks, for example fuel tanks in an aircraft, boat, train, car, etc.

The accumulation of contaminants in a fuel tank over time may lead to a need to monitor contamination levels to verify that the quantity of a contaminant does not exceed an acceptable limit, e.g. a performance threshold, and may periodically require action to be taken to reduce the quantity of the contaminant in the fuel tank. For example, moisture may enter an aircraft fuel tank during refueling and via its vent system, resulting in a need to periodically drain water from the fuel tank.

Fuel tank contamination levels may be measured directly at predetermined intervals to establish whether or not action should be taken to reduce contamination levels, for example by establishing whether or not the quantity of a contaminant in a fuel tank has reached an action level. Alternatively, action may be taken at predetermined intervals to reduce the contamination level regardless of the quantity of the contaminant present.

In the case of an aircraft fuel tank, a water drain maintenance activity is typically performed after a predetermined number of flight hours, or a predetermined number of flights, or a predetermined number of flights in a particular sector, e.g. tropics, arctic, etc., to account for the significant variation in the ambient humidity during the descent phase of a flight which affects the ingress of water via the fuel tank vent during descent.

Since the rate of accumulation of contaminants within a fuel tank is unlikely to be constant, and may be affected by one or more operating conditions, the intervals at which action should be taken in response to the accumulation of a contaminant is also unlikely to be constant. If maintenance tasks are conducted at predetermined intervals, this may result in unnecessary maintenance activities when a contaminant has accumulated at a slower than expected rate, which will increase operating costs and lead to unnecessary down time of the fuel system. In the case of a vehicle, for example an aircraft, this may require the vehicle to be out of service for longer than is necessary. In addition, time-based maintenance is ineffective at identifying problems which may develop between scheduled inspections.

In some industries, a technique called predictive maintenance (PdM) is used to decide when maintenance activities should occur. PdM tracks the performance or condition of an asset over time and uses this information to determine when maintenance activities will need to occur, therefore allowing maintenance activities to be planned in a cost and time effective manner. PdM can reduce costs and equipment down time compared to a conventional time-based and/or operation count-based maintenance approach.

SUMMARY OF THE INVENTION

A first aspect of the invention provides a method for predicting a quantity of a contaminant in a fuel tank at the end of a time period, the method comprising the steps of: determining a quantity of the contaminant in the fuel tank at the start of the time period; determining at least one operating condition of the fuel tank during the time period; using information relating to the at least one operating condition of the fuel tank to generate a predicted amount of accumulation of the contaminant in the fuel tank during the time period; and calculating, based upon the quantity of the contaminant at the start of the time period and the predicted amount of accumulation of the contaminant during the time period, a predicted quantity of the contaminant at the end of a time period.

A second aspect of the invention provides apparatus for generating a predicted quantity of a contaminant in a fuel tank at the end of a time period, the apparatus comprising a computer configured to: determine a quantity of the contaminant in the fuel tank at the start of the time period; determine at least one operating condition of the fuel tank during the time period; generate a predicted quantity of the contaminant accumulated in the fuel tank during the time period using information relating to the at least one operating condition of the fuel tank; and calculate, based upon the quantity of the contaminant at the start of the time period and the predicted quantity of the contaminant accumulated during the time period, a predicted quantity of the contaminant at the end of a time period.

The invention is advantageous in that it allows the quantity of a contaminant in a fuel tank to be predicted for a point in the future. This information may be useful for planning maintenance activities more accurately, for example by indicating when action should be taken to reduce the quantity of a contaminant in a fuel tank. This enables maintenance teams to plan their work efficiently as they are not required to work to a pre-determined schedule which may involve unnecessary maintenance activities if accumulation of a contaminant occurs at a slower than expected rate, therefore reducing operating costs and downtime.

The method may be used to predict the quantity of a contaminant at the end of a time period for a vehicle fuel tank, for example an aircraft, a train, a marine vessel or a road vehicle fuel tank. Alternatively the method may equally be used for any type of fuel tank, including stationary fuel tanks.

The operating condition used to generate the predicted amount of accumulation of the contaminant may be any condition which is believed to affect the rate of accumulation of the contaminant in the fuel tank. Alternatively, two or more operating conditions may be used. The operating condition(s) may be entered automatically or manually into a computer program or algorithm which uses the operating condition(s) to predict the accumulation of the contaminant during the time period.

The operating condition(s) used to predict the quantity of the contaminant accumulated in the fuel tank during the time period may include data relating to ambient conditions external to the fuel tank, for example ambient air temperature or pressure or humidity or a combination of these conditions, or internal fuel system factors such as the rate at which a water scavenge system delivers water to the engine(s). These conditions are known to affect the rate at which some contaminants accumulate in a fuel tank, and so may be particularly appropriate quantities to consider. However, other quantities may equally be used either separately or in conjunction with the quantities mentioned above if they are believed to affect the rate of accumulation.

Data relating to ambient air conditions may be directly measured or taken from a forecast or otherwise predicted. For example, in the case of an aircraft, temperature, pressure or humidity data may be: measured directly using sensors mounted on the aircraft; or measured at a take-off location by sensors outside the aircraft, flight destination or at any other location; or taken from a forecast; or predicted using average data from previous flights or periods of operation, or generated in any other way.

The prediction may be generated using a simulation of contaminant accumulation, or alternatively by extrapolating previous trends in contaminant accumulation, or by a combination of simulation and extrapolation.

To assist with predicting the rate or amount of accumulation during a time period, average data relating to operating conditions, or to the rate of accumulation of a contaminant, or to the quantity of a contaminant accumulated during a period of time may be used.

Average data relating to operating conditions may include average data for temperature or pressure or humidity or for any other condition believed to affect the accumulation of contaminants. For example, for a flight on a particular route, the operating conditions for the time period may be generated with the assistance of averaged data taken from similar flights, such as temperature or pressure or humidity data from flights with similar weather or ambient air conditions.

Average data relating to the rate of accumulation of a contaminant may include previously measured or determined rates of accumulation during similar time periods. For example, if it has previously been determined that a contaminant will accumulate in an aircraft fuel tank at a particular average rate when the aircraft is in a particular region and when ambient conditions are within a certain range, that average rate of accumulation may be applied to predict the accumulation on flights under similar conditions.

Average data relating to the quantity of a contaminant accumulated during a period of time may include previously measured or determined quantities accumulated during similar time periods. For example, the quantity of a contaminant assumed to be accumulated during a period under certain conditions may be taken as the average amount known to have been accumulated under similar conditions in previous flights.

It may also be desirable to predict the quantity accumulated during a particular event, for example a take off or landing event. In this case, the amount of the contaminant accumulated during an event may be taken as the average amount known to have been accumulated during similar events and under similar conditions in previous flights, for example the amount accumulated on average during a similar event in the same location when ambient air conditions are within a similar range.

The average data may further be specific to a particular route or sector, such that the predicted quantity accumulated during a time period over a particular route or in a particular sector is based on the quantity accumulated during comparable periods of operation. In this case, the quantity of the contaminant accumulated during a flight or generally during a time period or event may be taken as the average amount known to have accumulated during similar periods of operation under similar conditions in previous flights, for example the amount accumulated on average during a similar event in the same sector when ambient air conditions are within a similar range.

The method may use the position of the fuel tank to assist with predictions, for example GPS position data may be used to track the location of the fuel tank. This tracking may be used to record ambient conditions at particular location and/or to assist with determining ambient conditions based upon a weather forecast, for example.

The operating conditions may include a flight plan, which may be automatically entered or alternatively may be manually entered, for example by a pilot or a co-pilot before the start of a flight. The flight plan may include, for example, the departure and arrival locations, the route, the speed during the flight and the altitude. This information may also be used to generate more accurate data relating to the ambient air conditions external to the fuel tank, for example, the altitude of the aircraft during a period of time may affect the temperature and humidity.

The operating conditions may include ground conditions which affect the accumulation of water in the fuel tank when the aircraft is on the ground and/or data relating to maintenance activities or a refueling operation.

The contaminant may be water (in all its forms) including free water collected in a sump, water suspended or dissolved in fuel, and ice. The method may equally be used for other contaminants, for example oil, or any other fuel tank contaminant.

The predicted quantity of the contaminant at the end of the time period may be compared to a pre-determined quantity, for example a pre-determined action level. The action level may represent a level of a contaminant requiring a particular action to be taken, for example a maintenance task such as draining or otherwise removing a contaminant from the fuel tank. The method may, therefore, be used to plan when maintenance activities such as a water drain activity, for example, should occur.

At the end of the time period, the quantity of the contaminant in the fuel tank may be measured and compared to the predicted quantity of the contaminant according to the method described above. If the measured quantity of the contaminant in the fuel tank is significantly different to the predicted quantity, this may be taken as an indication that there is a fault with the fuel tank or a part of a fuel system.

The fuel tank may be provided with sensing means for measuring the quantity of the contaminant. When the contaminant is water, the sensing means may comprise a time domain reflectometry (TDR) probe. Alternatively, the sensing means may comprise any device suitable for measuring or otherwise determining the quantity of the contaminant in the fuel tank.

Data generated using the method may be transferred from the aircraft to outside the aircraft. The data transfer may occur wirelessly, with data being transmitted from the aircraft to a receiver located outside the aircraft, for example, to a computer used by a ground support crew. Alternatively data transfer may occur via a wired connection.

The method may be used to predict the quantity of a contaminant in a fuel tank, or alternatively the method may be used for more than one contaminant over a time period.

The method may be conducted using a plurality time periods to determine when maintenance activities should occur.

The initial prediction may be updated with real-time data during the time period to improve the accuracy of the prediction.

The apparatus may comprise a computer configured to generate a predicted amount of accumulation of a contaminant in a fuel tank during a time period using at least one operating condition of the fuel tank during the time period. The apparatus may further comprise a transmitter for wirelessly communicating the predicted quantity of the contaminant to an external receiver. Alternatively, the predicted quantity of the contaminant may be transmitted via a wired connection.

The apparatus may be installed on an aircraft and used to predict the quantity of the contaminant in a fuel tank of the aircraft at the end of the time period. Alternatively, the apparatus may be installed as part of a fuel system for any other fuel tank, for example a train, a marine vessel or a road vehicle fuel tank or a stationary fuel tank.

The apparatus may be configured to carry out any of the steps included in the method described above.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
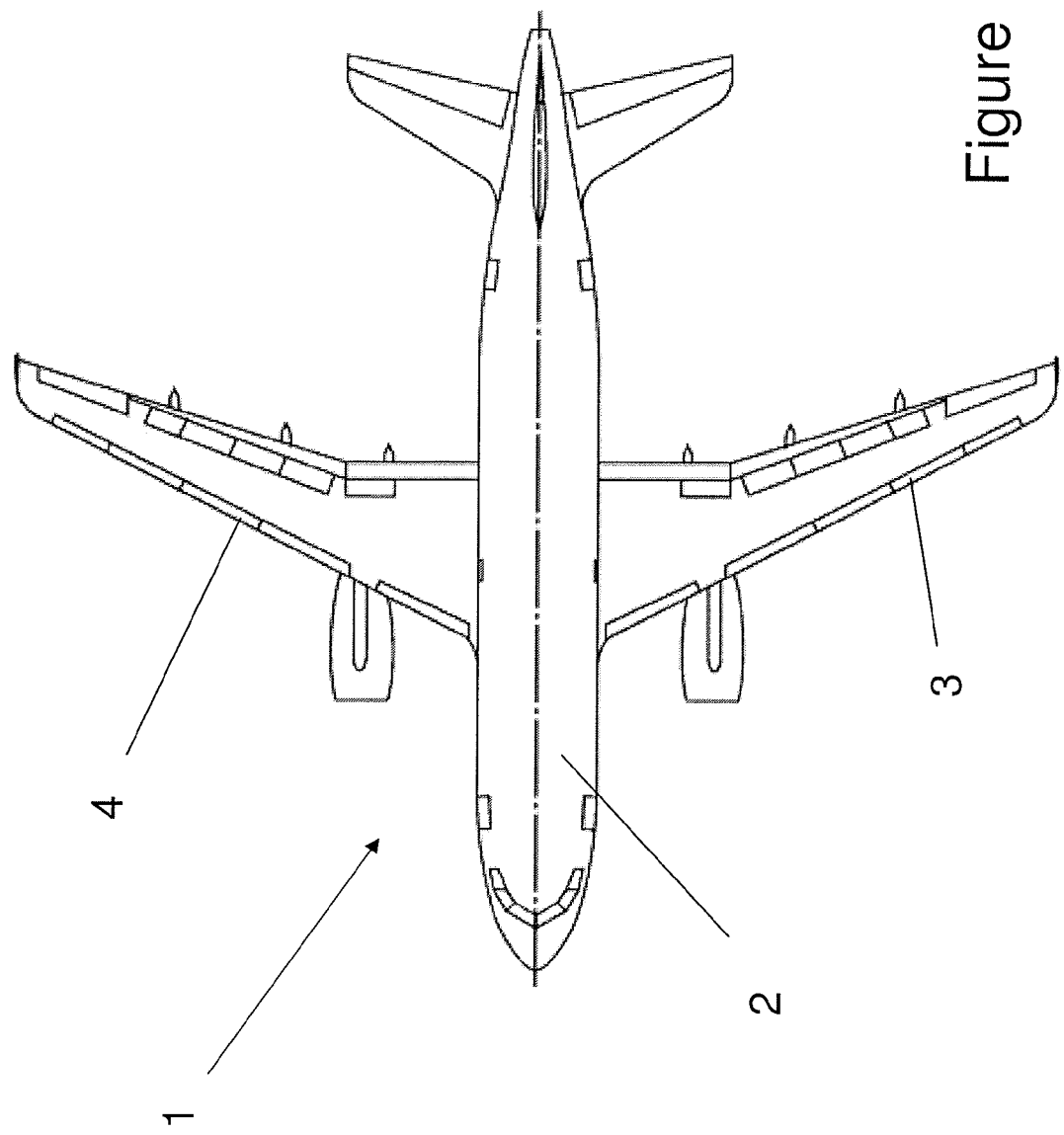
FIG. 1 shows a plan view of an aircraft having integral wing fuel tanks.

FIG. 1 shows a plan view of an aircraft 1 having a fuselage 2 and wings 3, 4. The aircraft has a fuel system including a fuel tank 5 (shown in FIG. 2) located within wing 3 which is used to store the fuel.

Figure 2:
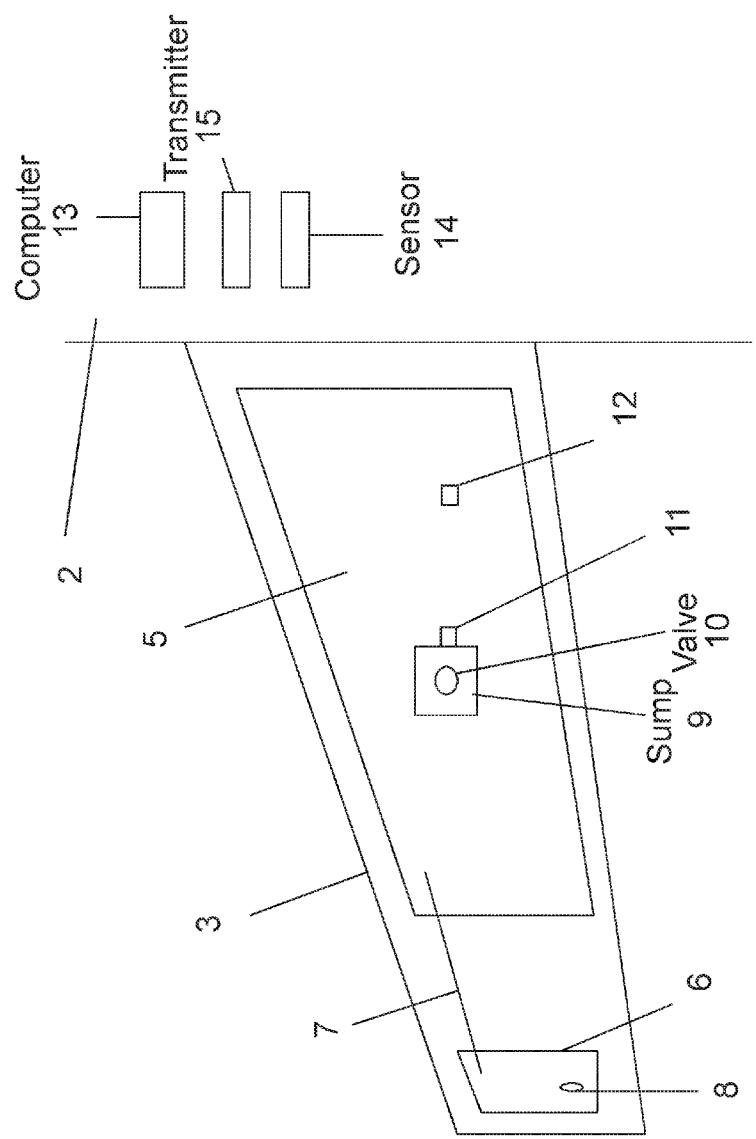
FIG. 2 shows a schematic view of the aircraft illustrating sensors in the fuel tank coupled to a contamination prediction system for predicting a quantity of a contaminant in the fuel tank.

FIG. 2 shows a schematic view of aircraft wing 3, having a fuel tank with a contamination prediction system. The fuel tank 5 is fluidically connected to a vent tank 6 by a vent line 7. The vent tank 6 has a vent duct 8 which is open to the ambient atmosphere on the underside of the wing to allow the movement of air into and out of the vent tank 6, therefore allowing pressure equalisation of the vent tank 6, and therefore also the fuel tank 5, with the ambient air. During flight, a slight positive pressure may be maintained within the fuel tank 5.

The air entering the fuel tank 5 via the vent duct 8 may contain moisture which may accumulate in the fuel tank. This is particularly relevant during the descent phase of a flight where the ambient pressure increases with decreasing altitude causing a net inflow of air into the fuel tank via the vent system. If the ambient air is relatively moist, e.g. in hot/wet climates, then this moisture may be accumulated in the fuel tank by condensing on the walls of the fuel tank 5 or dissolving in the fuel. The walls of the fuel tank are likely to be cold at the start of the descent from cruise altitude where the ambient temperature may be around minus 40 degrees Celsius. Additionally, water may enter the fuel tank, within controlled limits, during a refueling operation as water is almost always present as dissolved and free or suspended water in the fuel being delivered to the tank. The concentration of free or suspended water entering with the fuel is controlled by a filter through which the fuel passes during delivery to the fuel tank.

The presence of water in the aircraft fuel tank 5 is undesirable as it may lead to microbial contamination of the fuel tank. Microbial contamination may lead to increased wear and degradation of fuel system components, requiring the premature replacement or repair of some fuel system components.

Water which condenses onto the walls of the fuel tank 5 may fall to the bottom of the fuel tank 5 and be collected in a sump 9 located at a low point of the fuel tank 5, and sit below the fuel. There may be multiple water collecting sumps 9 within a single fuel tank.

Many aircraft fuel systems include a water scavenge system (not shown in the Figures) that scavenges water from the sump and delivers this to the aircraft engine(s) to be "burnt off" with the fuel. This is one way in which the concentration of water in the fuel tank is managed. However, the rate at which water may be fed to the engine(s) and the flight phases when this is allowed to occur are restricted and so over time the water collected in the sump will tend to rise, necessitating a water drain maintenance activity to ensure that the level of water in the sump is keep below a maximum limit.

Water may be drained from the sump 9 when the aircraft 1 is on the ground through a drain valve 10 by inserting a probe into the drain valve 10 which engages with the valve 10, opening it and allowing fluid to flow out of the fuel tank 5 through the drain valve 10 and into a collector bottle.

The draining of water from the fuel tank 5 may conventionally occur at set intervals, for example after a pre-determined number of days or a pre-determined number of flights in a particular sector, in order to prevent excessive build up of water within the fuel tank 5. However, this may result in unnecessary maintenance activities when water has accumulated in the sump at a slower than expected rate, increasing operating cost and down time of the aircraft.

The removal of moisture from a fuel tank may additionally be hampered by the presence of ice within the fuel system, since frozen water cannot be removed from the fuel tank 5 in the conventional way. Ice may form in the fuel tank at low temperatures, for example at cold cruise altitude temperatures or on the ground in cold locations. Ice may be removed from the fuel tank 5 by allowing the ice to melt, so that the water collects in the sump 9 and may be removed in the normal way. In cold environments, this may require the aircraft 1 to be left in a heated hanger to allow the ice to melt.

The fuel tank may further comprise a sensor 11 adapted to measure the amount of water collected at the bottom of the fuel tank 5 or in the sump 9 and a sensor 12 or sensors, for example a TDR probe, adapted to measure the concentration of dissolved and/or free (suspended) water in the fuel. An array of the sensors may be provided throughout the fuel tank(s), and only some of these may be submerged in the fuel (and therefore operational) at an instance depending on the fuel level within the tank(s). Alternatively, the sensing means may comprise any device suitable for measuring or otherwise determining the quantity of the contaminant in the fuel tank.

In one embodiment, the amount of water in the fuel tank 5 at the start of a time period is determined using sensors 11 and 12, which relay this information to a computer 13. The computer 13 then generates a predicted amount of water (in all its forms including liquid water, dissolved water in the fuel and ice) expected to be accumulated in the fuel tank 5 during a time period using operating conditions including the flight plan and flight profile and ambient conditions measured using sensors 14.

The computer 13 then adds the predicted amount of water that will be accumulated during the time period to the measured amount of water at the start of the time period to predict the quantity of water that will be inside the fuel tank 5 at the end of the time period.

During a flight, real-time on-board data is used to update the prediction as the measured quantities of water in the sump 9 and water dissolved in the fuel change and the operating conditions change to avoid accumulated error. The predicted quantity of water accumulated in the fuel tank 5 during the time period may rely on simulated data or may alternatively be generated by extrapolation from previously known rates of accumulation.

The predicted quantity is transmitted from the aircraft via a transmitter 15 to a computer (not shown) used for maintenance planning located outside the aircraft. This data is then used to help determine when it will be necessary to take action to remove water from the fuel tank 5 by the conventional water drain activity previously discussed. By repeating the prediction for several different time periods finishing at different points in time in the future, it is possible to estimate when the quantity of water in the fuel tank 5 or collected in sump 9 will reach a pre-determined level. This information is used to help plan a schedule for draining water form the sump 9.

The ability to predict the quantity of water in all its forms in a fuel tank at the end of time periods therefore allows a maintenance schedule to be prepared which specifies between which flights water should be drained from the sump 9 to ensure water levels do not exceed a predetermined quantity, while eliminating unnecessary maintenance activities. By predicting the total quantity of water in all its forms in the fuel tank it is also possible to estimate the quantity of water that may be retained within the fuel tank, i.e. water that is not free water, such as ice and dissolved water at a particular fuel temperature. This may be beneficial where the quantity of ice, for example, is not directly measurable.

In addition, if the readings from the sensors 11, 12 indicate that water is accumulating in the fuel tank 5 at a significantly faster than expected rate as predicted by the computer 13, this may be taken as an indication that there is a fault with a part of the fuel system or prediction system described. For example, it may indicate a fault with the fuel tank 5, or sensors 11, 12, or computer 13 or with any other component or system which interacts with any part of the fuel system. In this case it may be necessary for a ground support team to analyse the fuel system to check for faults.

Figure 3:
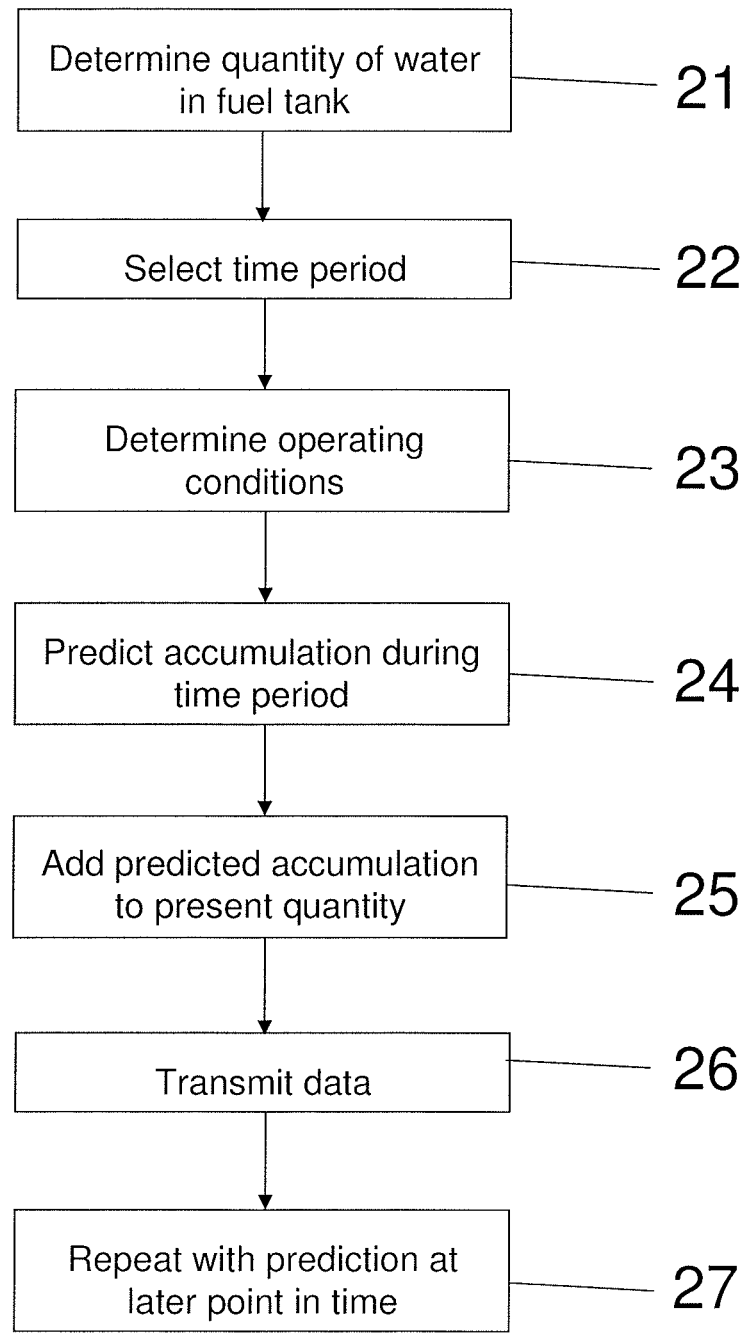
FIG. 3 is a block diagram showing the steps of a method followed by a computer of the contamination prediction system.

FIG. 3 is a block diagram showing the steps followed by a computer 13 in an embodiment to estimate and transmit a predicted quantity of water accumulated in the sump 9 to a ground support crew.

Block 21 represents the step of measuring the quantity of water in the fuel tank 5 using sensors 11, 12 to determine the quantity of water collected in the sump and suspended in the fuel at the start of a time period.

Block 22 represents the step of selecting a time period over which to estimate the accumulation of water in the sump 9, allowing an estimate of the quantity of water in the sump 9 at the end of the time period to be generated.

Block 23 represents the step of measuring or otherwise determining operating conditions which are believed to affect the rate of accumulation of water in the sump 9. The operating conditions may include temperature, pressure and humidity as measured by sensors 14, water scavenge rate, a flight plan entered into the computer 13 by a pilot and predicted ascent, cruise, decent and fuel burnt profiles.

Block 24 represents the step of predicting the quantity of water accumulated in the fuel tank 5 during the time period, using the operating conditions to determine the accumulation during the time period through simulation and extrapolation of data from previous periods of operation. The predicted accumulation may be generated by simulation when appropriate operating conditions (see block 23) are available, or may be generated by extrapolation of the previous trends if the desired input data is not available. Simulation may provide a better forecast than extrapolation.

Block 25 represents the step of adding the predicted quantity of water accumulated in the sump 9 during the time period to the measured quantity at the start of the time period to generate a prediction of the quantity of water in the sump 9 at the end of the time period.

Block 26 represents the step of transmitting the predicted quantity of water in the sump 9 at the end of the time period from transmitter 15 to a computer (not shown) used for maintenance planning located outside the aircraft.

Block 27 represents the step of repeating the process at a later point in time before the end of the time period for a second time period ending at the same point as the first time period to generate an updated prediction of the quantity of water in the sump 9 at the end of the time period, and transmitting this data to a computer used by a ground support crew.

The above described embodiment is a non limiting example of the invention. The method and apparatus described in the appended claims may be adapted to predict the quantity of water, or dissolved water, or ice, or water in all its forms, or another contaminant in any fuel tank at the end of any time period.

The fuel tank may be located in an aircraft wing as described; or alternatively in another part of an aircraft; or may be any type of stationary fuel tank, for example a storage tank or a generator fuel tank; or any type of vehicle fuel tank, for example a fuel tank in an aircraft or boat or train or car.

The quantity of the contaminant at the start of the time period may be determined by measuring or may alternatively be determined by some other means. For example, when the contaminant is water and the time period starts shortly after a draining operation, it may be appropriate to assume that there is substantially no free water in the fuel tank at the start of the time period. Alternatively, when the contaminant is ice and the time period starts after the fuel tank has been in a warm environment for an extended period of time, it may be appropriate to assume that there is no ice in the fuel tank at the start of the time period. Alternatively the quantity of the contaminant at the start of the time period may be estimated or simulated in some other way.

The time period may extend throughout a particular period of use, for example, when the method is applied to an aircraft fuel tank, the start of the time period may be shortly before the aircraft takes off at the start of a flight and the end of the time period may be when the aircraft lands at the end of the flight. However, the time period may cover any period of time and may be of any length. For example, when the method is applied to an aircraft fuel tank, the time period may extend across several flights, or only a part of a flight, or cover a period in which the aircraft is on the ground.

The operating conditions listed in the preferred embodiments have been selected for illustrative purposes; a predicted amount of accumulation of a contaminant during a time period may be generated using any suitable selection of operating condition(s) believed to affect the rate of accumulation of a contaminant, and may include all, or some, or none of the operating conditions listed in the preferred embodiments.

The predicted quantity of the contaminant at the end of the time period may be transmitted wirelessly to an external receiver as described in the preferred embodiments, or may alternatively be transmitted via a wired connection, or may not be transmitted to an external computer.

Although the invention has been described above with reference to specific preferred embodiments, it will be appreciated that various changes or modifications may be made without departing from the scope of the invention as defined in the appended claims.

What is claimed is:

1. A method for predicting a quantity of a contaminant in a fuel tank at the end of a time period, the method comprising the steps of:
   determining a quantity of the contaminant in the fuel tank at the start of the time period;
   determining at least one operating condition of the fuel tank during the time period which affects the quantity of the contaminant in a known manner;
   using information relating to the at least one operating condition of the fuel tank to generate a predicted quantity of the contaminant accumulated in the fuel tank during the time period; and
   calculating, based upon the quantity of the contaminant at the start of the time period and the predicted quantity of the contaminant accumulated during the time period, a predicted quantity of the contaminant at a future point of time at the end of a time period.

2. A method according to claim 1 wherein the contaminant is water.

3. A method according to claim 1 wherein the predicted quantity of the contaminant at the end of the time period is transferred to outside the aircraft.

4. A method according to claim 1 wherein the method is used to predict the quantity of two or more contaminants in a fuel tank at the end of a time period.

5. A method according to claim 1 wherein predicted quantities of the contaminant are calculated for multiple time periods having different end points.

6. Use of a method according to claim 1 to determine when maintenance activities should occur.

7. A method according to claim 1 wherein the fuel tank is a vehicle fuel tank.

8. A method according to claim 7 wherein the vehicle is an aircraft.

9. A method according to claim 1 wherein the operating conditions include ambient air conditions outside the fuel tank.

10. A method according to claim 9 wherein the ambient air conditions include at least one quantity selected from a group including temperature, pressure and humidity.

11. A method according to claim 8 wherein one of the operating conditions is a flight plan.

12. A method according to claim 11 wherein the flight plan is entered manually.

13. A method according to claim 1 wherein the predicted quantity of the contaminant at the end of the time period is compared to a predetermined quantity.

14. A method according to claim 13 wherein the predetermined quantity is an action level.

15. A method according to claim 1 wherein the quantity of the contaminant in the fuel tank is measured at the end of the time period.

16. A method according to claim 15 wherein the measured quantity of the contaminant is compare to the predicted quantity of the contaminant at the end of the time period.

17. Apparatus for generating a predicted quantity of a contaminant in a fuel tank at the end of a time period, the apparatus comprising a computer configured to:
   determine a quantity of the contaminant in the fuel tank at the start of the time period;
   determine at least one operating condition of the fuel tank during the time period which affects the quantity of the contaminant in a known manner;
   generate a predicted quantity of the contaminant accumulated in the fuel tank during the time period using information relating to the at least one operating condition of the fuel tank; and
   calculate, based upon the quantity of the contaminant at the start of the time period and the predicted quantity of the contaminant accumulated during the time period, a predicted quantity of the contaminant at a future point of time at the end of a time period.

18. Apparatus according to claim 17 further comprising a transmitter for communicating the predicted quantity of the contaminant in the fuel tank at the end of the time period to an external receiver.

19. Apparatus according to claim 17 further comprising a sensor for measuring the quantity of the contaminant in the fuel tank at the start of the time period.

20. An aircraft comprising a fuel tank and apparatus for generating a predicted quantity of a contaminant in a fuel tank at the end of a time period, the apparatus comprising a computer configured to:
   determine a quantity of the contaminant in the fuel tank at the start of the time period;
   determine at least one operating condition of the fuel tank during the time period that affects the quantity of the contaminant in a known manner;
   generate a predicted quantity of the contaminant accumulated in the fuel tank during the time period using information relating to the at least one operating condition of the fuel tank; and
   calculate, based upon the quantity of the contaminant at the start of the time period and the predicted quantity of the contaminant accumulated during the time period, a predicted quantity of the contaminant at a future point of time at the end of a time period.

* * * * *